US009056151B2

(12) United States Patent
Lauritzen et al.

(10) Patent No.: US 9,056,151 B2
(45) Date of Patent: Jun. 16, 2015

(54) METHODS FOR COLLAGEN PROCESSING AND PRODUCTS USING PROCESSED COLLAGEN

(75) Inventors: Nels J. Lauritzen, Piscataway, NJ (US); Lawrence A. Shimp, Morganville, NJ (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 1667 days.

(21) Appl. No.: 11/673,972

(22) Filed: Feb. 12, 2007

(65) Prior Publication Data

US 2008/0195202 A1 Aug. 14, 2008

(51) Int. Cl.
A61L 15/32 (2006.01)
A61L 27/54 (2006.01)
A61L 27/24 (2006.01)
A61L 27/34 (2006.01)

(52) U.S. Cl.
CPC ............. *A61L 27/54* (2013.01); *A61L 15/325* (2013.01); *A61L 27/24* (2013.01); *A61L 27/34* (2013.01); *A61L 2300/00* (2013.01)

(58) Field of Classification Search
CPC ...... A61K 38/39; C07K 14/78; A61L 15/325; A61L 17/08; A61L 24/102; A61L 26/0033; A61L 27/24; A61L 27/36; A61L 29/36; A61L 29/045; A61L 31/044; A61L 33/122
See application file for complete search history.

(56) References Cited

U.S. PATENT DOCUMENTS

| | | | |
|---|---|---|---|
| 3,276,448 A | 10/1966 | Kronenthal | |
| 3,366,440 A | 1/1968 | Nuwayser | |
| 4,060,081 A | 11/1977 | Yannas et al. | |
| 4,089,333 A | 5/1978 | Utsuo et al. | |
| 4,215,693 A | 8/1980 | Rothman et al. | |
| 4,233,360 A | 11/1980 | Luck et al. | |
| 4,440,750 A | 4/1984 | Glowacki et al. | |
| 4,621,631 A | 11/1986 | Paques et al. | |
| 4,642,118 A | 2/1987 | Kuroyanagi et al. | |
| 4,657,548 A * | 4/1987 | Nichols ........................... 623/10 |
| 4,725,671 A | 2/1988 | Chu et al. | |
| 4,803,075 A | 2/1989 | Wallace et al. | |
| 4,841,962 A | 6/1989 | Berg et al. | |
| 4,937,323 A | 6/1990 | Silver et al. | |
| 4,956,178 A | 9/1990 | Badylak et al. | |
| 4,963,146 A | 10/1990 | Li | |
| 5,043,426 A | 8/1991 | Goldstein | |
| 5,064,941 A | 11/1991 | Davison | |
| 5,116,389 A | 5/1992 | Mitz | |
| 5,133,755 A | 7/1992 | Brekke | |
| 5,138,030 A * | 8/1992 | Pachence ...................... 530/356 |
| 5,141,747 A | 8/1992 | Scholz | |
| 5,162,430 A | 11/1992 | Rhee et al. | |
| 5,207,705 A | 5/1993 | Trudell et al. | |
| 5,282,859 A | 2/1994 | Eisenberg | |
| 5,350,583 A | 9/1994 | Yoshizato et al. | |
| 5,378,469 A | 1/1995 | Kemp et al. | |
| 5,428,022 A * | 6/1995 | Palefsky et al. ................. 514/21 |
| 5,436,135 A | 7/1995 | Tayot et al. | |
| 5,523,291 A | 6/1996 | Janzen et al. | |
| 5,532,217 A | 7/1996 | Silver et al. | |
| 5,554,389 A | 9/1996 | Badylak et al. | |
| 5,595,571 A | 1/1997 | Jaffe et al. | |
| 5,607,590 A | 3/1997 | Shimizu | |
| 5,618,312 A | 4/1997 | Yui et al. | |
| 5,658,593 A | 8/1997 | Orley et al. | |
| 5,716,411 A | 2/1998 | Orgill et al. | |
| 5,814,328 A | 9/1998 | Gunasekaran | |
| 5,837,278 A | 11/1998 | Geistlich et al. | |
| 5,855,619 A | 1/1999 | Caplan et al. | |
| 5,861,034 A | 1/1999 | Taira et al. | |
| 5,948,426 A | 9/1999 | Jefferies | |
| 5,997,895 A | 12/1999 | Narotam et al. | |
| 6,022,557 A | 2/2000 | Maser | |
| 6,057,148 A | 5/2000 | Sugiyama et al. | |
| 6,080,194 A | 6/2000 | Pachence et al. | |
| 6,179,872 B1 | 1/2001 | Bell et al. | |
| 6,277,397 B1 * | 8/2001 | Shimizu ......................... 424/443 |

(Continued)

FOREIGN PATENT DOCUMENTS

| | | |
|---|---|---|
| WO | WO-85/05274 | 12/1985 |
| WO | WO-96/31157 | 10/1996 |
| WO | WO-00/35375 | 6/2000 |
| WO | WO-2008/100967 | 8/2008 |

OTHER PUBLICATIONS

Montesano et al. "Basic fibroblast growth factor induces angiogenesis in vitro" Proc. Nati. Acad. Sci. USA vol. 83, pp. 7297-7301, Oct. 1986.*
Brown P. et al., "Sodium Hydroxide Decontamination of Creutzfeld-Jakob Disease Virus", *The New England Journal of Medicine*, vol. 310, No. 11, 1 p.
"Bioelevation™—Ptosis Slings (Brow Suspension Surgery)", *Surgeons & Med Professionals*, © 2007 IOP, Inc., 2 pp.
Hinton, R. et al., "A biomechanical analysis of solvent-dehydrated and freeze-dried human fascia lata allografts", *The American Journal of Sports Medicine*, vol. 20, No. 6, © 1992, pp. 607-612.

(Continued)

*Primary Examiner* — Christina Bradley
(74) *Attorney, Agent, or Firm* — Sorell Lenna & Schmidt LLP

(57) ABSTRACT

Purifying human derived collagen from human tissue includes treating harvested human tissue with an enzyme to form a collagen product, deactivating the enzyme with a non-alkaline enzyme deactivation solution, and collecting the collagen product resulting from the enzyme treatment, where the collected collagen product includes a preserved amount of its natural collagen constituents. Various medical implants can be formed using the isolated, enzymatically-treated human derived collagen having an amount of its natural collagen constituents preserved, and may include implantable sponges, patches, tubes, structural supports and coatings, and which may be used for repair, barrier, support and/or stabilization purposes.

21 Claims, 8 Drawing Sheets

(56) References Cited

U.S. PATENT DOCUMENTS

| | | | |
|---|---|---|---|
| 6,290,718 B1 * | 9/2001 | Grooms et al. | 623/1.15 |
| 6,391,333 B1 | 5/2002 | Li et al. | |
| 6,417,166 B2 | 7/2002 | Liu | |
| 6,440,167 B2 | 8/2002 | Shimizu | |
| 6,444,222 B1 | 9/2002 | Asculai et al. | |
| 6,455,309 B2 | 9/2002 | Stone | |
| 6,485,723 B1 | 11/2002 | Badylak et al. | |
| 6,500,464 B2 | 12/2002 | Ceres et al. | |
| 6,514,514 B1 * | 2/2003 | Atkinson et al. | 424/423 |
| 6,599,323 B2 | 7/2003 | Melican et al. | |
| 6,599,524 B2 | 7/2003 | Li et al. | |
| 6,658,626 B1 | 12/2003 | Aiken | |
| 6,682,760 B2 | 1/2004 | Noff et al. | |
| 6,685,626 B2 | 2/2004 | Wironen | |
| 6,699,287 B2 | 3/2004 | Son et al. | |
| 6,713,085 B2 | 3/2004 | Geistlich et al. | |
| 6,733,787 B2 | 5/2004 | Peterson et al. | |
| 6,752,834 B2 | 6/2004 | Geistlich et al. | |
| 6,753,311 B2 | 6/2004 | Fertala et al. | |
| 6,790,454 B1 | 9/2004 | Abdul Malak et al. | |
| 6,855,860 B2 | 2/2005 | Ruszczak et al. | |
| 6,893,462 B2 | 5/2005 | Buskirk et al. | |
| 6,893,653 B2 | 5/2005 | Abraham et al. | |
| 6,932,833 B1 | 8/2005 | Sandoval et al. | |
| 6,939,562 B2 | 9/2005 | Spiro et al. | |
| 6,969,523 B1 * | 11/2005 | Mattern et al. | 424/423 |
| 6,977,231 B1 | 12/2005 | Matsuda | |
| 7,004,977 B2 | 2/2006 | Ashman | |
| 7,025,739 B2 | 4/2006 | Saul | |
| 7,025,742 B2 | 4/2006 | Rubenstein et al. | |
| 7,029,689 B2 | 4/2006 | Berglund et al. | |
| 7,041,868 B2 | 5/2006 | Greene et al. | |
| 7,084,082 B1 | 8/2006 | Shimizu | |
| 7,141,072 B2 | 11/2006 | Geistlich et al. | |
| 7,147,871 B2 | 12/2006 | Voytik-Harbin et al. | |
| 7,153,518 B2 | 12/2006 | Wironen et al. | |
| 7,189,221 B2 | 3/2007 | Silverberg et al. | |
| 7,201,917 B2 | 4/2007 | Malaviya et al. | |
| 7,204,825 B2 | 4/2007 | Cimino et al. | |
| 7,226,611 B2 | 6/2007 | Yura et al. | |
| 7,232,411 B2 | 6/2007 | Dinkler, II et al. | |
| 2001/0053839 A1 | 12/2001 | Noishiki et al. | |
| 2002/0103542 A1 | 8/2002 | Bilbo | |
| 2003/0114061 A1 | 6/2003 | Matsuda et al. | |
| 2004/0001877 A1 | 1/2004 | Li et al. | |
| 2004/0013712 A1 | 1/2004 | Parma | |
| 2004/0034374 A1 | 2/2004 | Zatzsch et al. | |
| 2005/0065616 A1 | 3/2005 | Ankorina-Stark et al. | |
| 2005/0125077 A1 * | 6/2005 | Harmon et al. | 623/23.72 |
| 2005/0142161 A1 | 6/2005 | Freeman et al. | |
| 2005/0260251 A1 | 11/2005 | Hiltner et al. | |
| 2005/0267527 A1 | 12/2005 | Sandoval et al. | |
| 2005/0283256 A1 | 12/2005 | Sommerich et al. | |
| 2006/0088578 A1 | 4/2006 | Li et al. | |
| 2006/0093644 A1 | 5/2006 | Quelle et al. | |
| 2006/0147501 A1 | 7/2006 | Hillas et al. | |
| 2006/0159731 A1 | 7/2006 | Shoshan | |
| 2006/0167561 A1 | 7/2006 | Odar et al. | |
| 2006/0184098 A1 | 8/2006 | Barnitz et al. | |
| 2006/0235306 A1 | 10/2006 | Cotter et al. | |
| 2006/0252981 A1 | 11/2006 | Matsuda et al. | |
| 2006/0286144 A1 | 12/2006 | Yang et al. | |
| 2006/0293760 A1 | 12/2006 | DeDeyne | |
| 2007/0009585 A1 | 1/2007 | Morinaga et al. | |
| 2007/0021704 A1 | 1/2007 | Hariri et al. | |
| 2007/0027414 A1 | 2/2007 | Hoffman et al. | |
| 2007/0073415 A1 | 3/2007 | Sommerich | |
| 2007/0088445 A1 | 4/2007 | Patel et al. | |
| 2007/0098755 A1 | 5/2007 | Patel et al. | |
| 2007/0154515 A1 | 7/2007 | Johnson et al. | |
| 2007/0161109 A1 | 7/2007 | Archibald et al. | |
| 2008/0050417 A1 | 2/2008 | Dufrane et al. | |
| 2008/0260794 A1 | 10/2008 | Lauritzen et al. | |
| 2009/0306790 A1 | 12/2009 | Sun | |
| 2009/0311298 A1 | 12/2009 | Nixon et al. | |
| 2009/0312524 A1 | 12/2009 | Lauritzen | |
| 2010/0028309 A1 | 2/2010 | Odar et al. | |

OTHER PUBLICATIONS

Abe et al., "Clinical Experiences with Solvent-Dried Fascia Lata in Plastic Surgery", *Jap. Journal Plast. Reconst. Surg.*, 1991, vol. 11, pp. 721-730.

Guo, C. et al. "Flow and Magnetic Field Induced Collagen Alignment", *Biomaterials 28*, pp. 1105-1114 (2007).

Zerris, V. et al., "Repair of the Dura Mater with Processed Collagen Devices", *Journal of Biomedical Materials Research Part B: Appl Biomater* 83B: 580-588 (2007).

Nakata, K., et al., "Reconstruction of the lateral ligaments of the ankle using solvent-dried and gamma irradiated allogenic fascia lata", *The Journal of Bone and Joint Surgery*, vol. 82-B, No. 4, 4pgs. (May 2000).

Derwin, K., et al., "Regional variability, processing methods, and biophysical properties of human fascia lata extra cellular matrix", *Wiley Periodicals*, pp. 500-507 (2007).

Freytes, D. et al., "Unixial and Biaxial Properties of Terminally Sterilized Porcine Urinary Bladder Matrix Scaffolds", *Journal Biomed Mater Res part B: Appln Biomater 84B*, pp. 408-414 (2008).

Hodde, Jason, "Naturally Occurring Scaffolds for Soft Tissue Repair and Regeneration", *Tissue Engineering*, vol. 8, No. 2, pp. 295-308, (2002).

Gouk, S. et al., *Alterations of human acellular tissue matrix by gamma irradiation: Histology, Biomedical Materials Research Part B: Applied Biomaterials*, 16 pgs. (2007).

Burgeson, R., et al., "Collagen Types Molecular Structure and Tissue Distribution", *Basic Science and Pathology*, pp. 250-272, (1991).

Bigaré, A. et al., "Clinical Application of Human Acellular Collagen Matrix as a Dural Substitute", University Tissue Bank and Department of Neurosurgery, 1pg.

Dufrane, D. et al., "Clinical application of a physically and chemically processed human substitute for dura mater" *J. Neurosurg* 98, pp. 1198-1202, (2003).

Dufrane D., et al., "Physical and Chemical Processing for a human dura mater substitute", *Biomaterials* 23 pp. 2979-2988 (2002).

Burres, Steven, "Preserved Particulate Fascia Lata for Injection: A New Alternative", *Dermatol Surg* vol. 25 Oct. 1999, 790-794.

Hegedus, et al., "Non-Surgical Treatment Modalities of Facial Photodamage: Practical Knowledge for the Oral and Maxillofacial Professional", *International Journal of Oral and Maxillofacial Surgery* Copenhagen, Denmark, vol. 35, No. 5 May 1, 2006, 389-398.

Zeugolis, D.I. et al. "Factors influencing the properties of reconstituted collagen fibers prior to self-assembly: Animal species and collagen extraction method," *Wiley InterScience*, published online Nov. 27, 2007 (www.interscience.wiley.com).

* cited by examiner

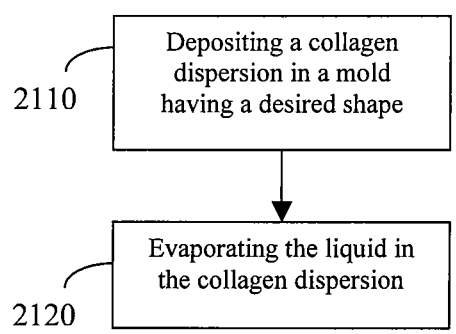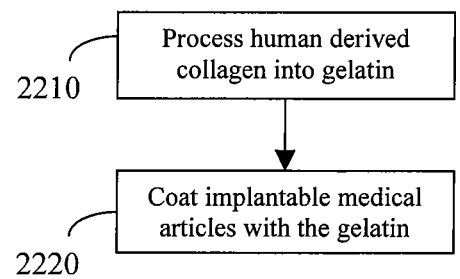
Fig. 2E
Fig. 2F

METHODS FOR COLLAGEN PROCESSING AND PRODUCTS USING PROCESSED COLLAGEN

FIELD OF THE INVENTION

The invention relates generally to a method for recovering collagen from human tissue and uses thereof. More particularly, the invention relates to processing human tissue to preserve human collagen fiber having its uniquely human biological characteristics, and use of the preserved collagen fibers in medical implants.

BACKGROUND

Collagen is used as an implant material to replace or augment hard or soft connective tissue, such as skin, tendons, cartilage, and bone. Some implants are formed as solid, flexible, or deformable collagen masses cross-linked with chemical agents, radiation, or other means to improve mechanical properties, decrease the chance of an immunogenic response, and/or to manage the resorption rate.

Collagen used in medical implants for implantation in humans generally has been of a nonhuman origin, i.e., xenogenic. A problem with the use of xenogenic tissue as a starting material when generating medical implants is that the tissue may be contaminated with viruses or prions. For example, products using bovine sourced tissue have the potential for transmitting BSE (Bovine Spongiform Encephelothopoly). As a result, xenogenic tissue is subjected to one or more processes intended to remove prions or other harmful contaminants. For example, treatment of collagen with an alkali solution has been used to remove harmful and undesirable contaminants from collagen. However, subjecting collagen to an alkali environment is harsh on the collagen tissue and can tend to unnecessarily degrade it.

Another problem with the use of xenogenic tissue is the potential for inflammation responses, hematomas, adhesions, and rejection after implantation. This is because xenogenic collagen includes constituents, such as telo-peptides, that can initiate an immunogenic response in humans. Processing methods for removing telo-peptides from collagen may help in product acceptance into the body. However, even with the removal of the telo-peptides, the implant may be reacted to (i.e., inflammation) and/or rejected due to the xenogenic nature of the collagen or due to irregular or damaged forms of proteins or other materials being revealed that are not recognized by the implantee's biochemistry. Further, processing methods effective in removing telo-peptides or other immunogenic-inducing portions of collagen may degrade the collagen, including by stripping away other portions of the collagen capable of providing potential benefits.

Thus, there is a need for methods for processing collagen, including human collagen, that avoid risks of contamination or infection with foreign pathogens. There also is a need for methods for processing collagen, including human collagen, that addresses constituents that can cause an immunogenic response in humans. There also is a need for methods for processing collagen, including human collagen, that avoid excessive degradation of the collagen. There further is a need for medical products made from the collagen processed by these methods.

SUMMARY

Methods for recovering collagen from tissue, and medical implants using the same, are provided. More specifically, methods for recovering human derived collagen fibers are provided, along with a method and apparatus providing medical implants having human derived collagen.

In one embodiment, a method for purifying human derived collagen includes treating harvested human tissue with an enzyme to form a collagen product; deactivating the enzyme with a non-alkaline enzyme deactivation solution; and collecting the collagen product resulting from the enzyme treatment, where the collected collagen product includes a preserved amount of its natural collagen constituents.

In other embodiments, a medical implant is provided that includes isolated, enzymatically-treated human derived collagen having an amount of its natural collagen constituents preserved. The medical implants may take various forms and may include sponges, patches, tubes, structural supports and coatings, threads, woven and non-woven constructs, and other configurations that may be used for repair, barrier, support and/or stabilization purposes.

Other features and advantages of the invention will become apparent from the following detailed description, taken in conjunction with the accompanying drawings, which illustrate, by way of example, various features of embodiments of the invention.

DESCRIPTION OF THE DRAWINGS

FIGS. 2A-2E depict methods of forming a medical implant using human derived collagen according to certain embodiments of the invention.

FIG. 2F depicts methods of forming a medical implant using human derived collagen as a coating according to certain embodiments of the invention.

DETAILED DESCRIPTION

Collagen accounts for approximately 30% of the human body. The present invention discloses methods for harvesting and processing human collagen into collagen-based or collagen-containing medical implants that have such properties as being one or more of physiologically compatible, sufficiently noninfectious to prevent transmission of viruses and prions, pliable, available for a wide variety of applications in a variety of shapes and sizes, high in tensile strength, and inert. The present application also is directed to implants made as a result of such methods. At least 26 collagen types in the human body are presently known, each of which adds specific function(s) to the collagen's structural role. Therefore, a variety of types of human tissue may be processed to yield human derived collagen fibers. In particular, type I collagen found in tendons and the pericardium, type III collagen found in intestines, type I or III collagen from fascia, and type V collagen found in interstitial tissue are some examples of starting materials that may be used for recovering human derived collagen fibers.

While the present disclosure is written primarily in terms of human tissue and human collagen, it is understood that the methods may be used in any appropriate context with any appropriate material, including xenogenic collagen and other mammalian tissues. In addition, although the methods and products described below involve human collagen, the present invention is directed to any type of tissue. It also is directed to any type of tissue that may be implanted in an allogenic context. For example, equine collagen may be processed and used for equine implantation, canine collagen may be processed and used for canine implantation, etc. The use of tissue for implantation from the same species source can provide benefits due to the potential of the natural constituents, unique to the species, providing implantation benefits once implanted. For example, a biochemical response in the implantee recognizing the natural constituents in the implant as acceptable may facilitate biological processes such as cross-linking and integration.

Collagen can be harvested from human tissue using various methods in accordance with the present invention. In some embodiments, preparation of human collagen for use in various medical implants involves enzyme treatment of harvested human tissue to separate collagen fibers in tissue from other components, and to break down peptide bonds between amino acids of proteins in the collagen, while retaining the native, uniquely human biological characteristics and receptivity of the human derived collagen. Once recovered, the collagen may be further processed based on the collagen's intended use.

Figure 1A:
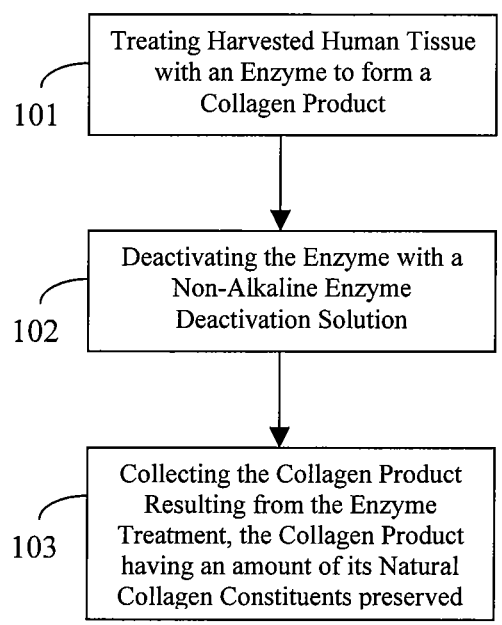
FIG. 1A depicts methods for recovering human derived collagen from human tissue according to certain embodiments of the invention.

FIG. 1A depicts a method for preserving human derived collagen from harvested human tissue according to certain embodiments of the invention. According to FIG. 1A, the method includes treating (101) harvested human tissue with an enzyme to form a collagen product. The enzyme is deactivated (102) using a non-alkaline enzyme deactivation solution, and the collagen product resulting from the enzyme treatment is then collected (103). The resulting collagen product, according to embodiments of the present invention, includes a preserved amount of its natural collagen constituents. By a "preserved amount," it is meant that the resulting processed collagen retains a sufficient amount or effective amount of the original or native collagen structure and/or constituents to be suitable or therapeutically useful for the collagen's intended application.

Figure 1B:
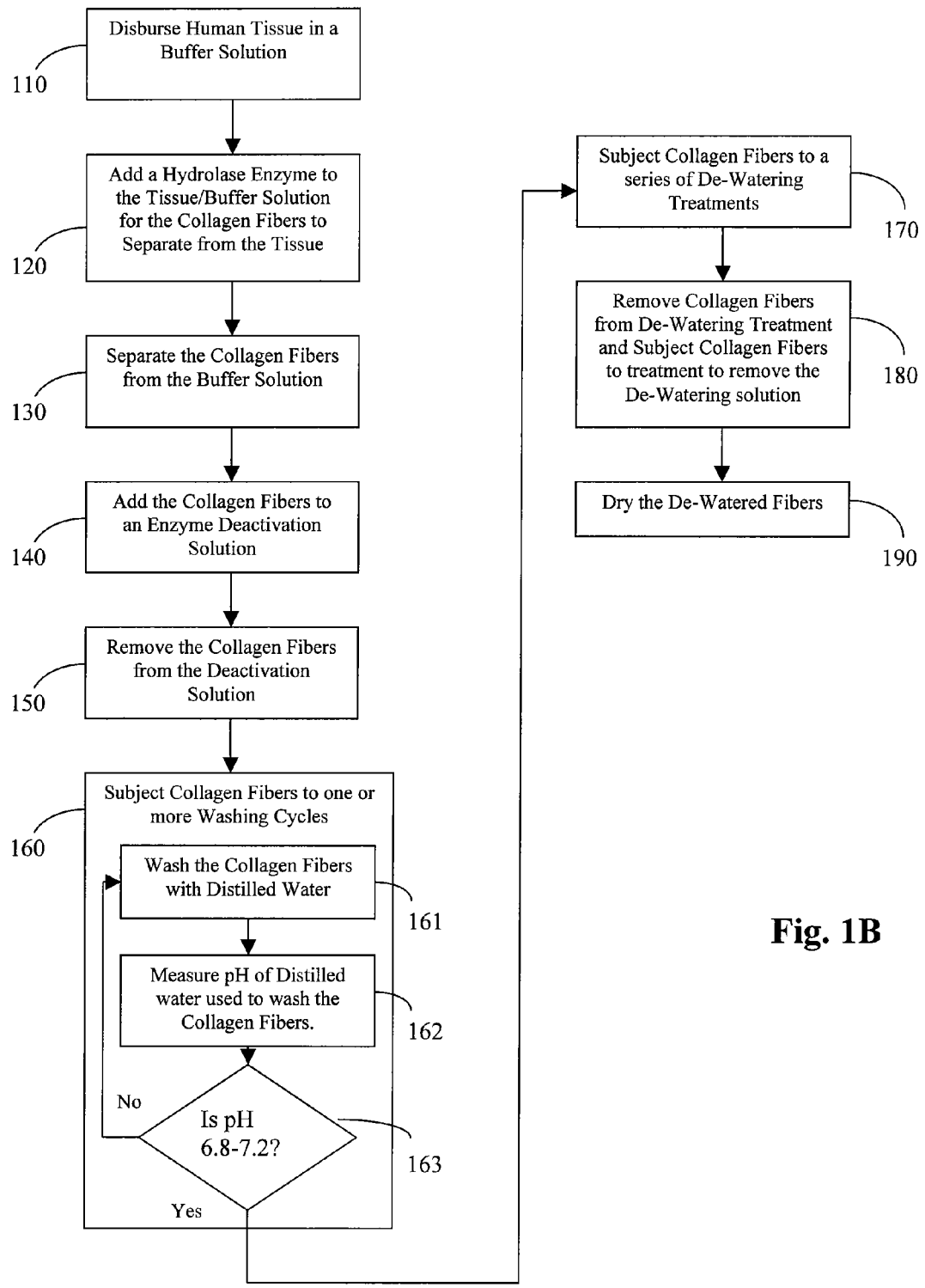
FIG. 1B depicts methods for recovering human derived collagen from human tissue according to certain embodiments of the invention.

FIG. 1B depicts a more detailed collagen preservation method according to certain embodiments of the present invention. According to one method, finely ground or sliced human tissue (such as fascia, tendon, and/or small intestine submucosa) containing bound collagen is disbursed (110) in a buffer solution at a suitable temperature and pH. Any suitable buffer solution at any appropriate pH and temperature may be used for providing an environment for the efficient use of a particular enzyme to enable the enzyme to attack and remove material. In the exemplary use of ficin in a buffer solution of potassium phosphate ($KH_2PO_4$) and sodium hydroxide (NaOH), enzymatic activity is carried out efficiently at a pH of 6.3±0.15 and at a temperature of 37° C.±1.5° C. However, it will be understood that buffer solutions may be suitable at any appropriate pH, such as a pH from about 3 to about 9, from about 5 to about 7, or from about 6.0 to about 6.3. Further, buffer solutions may be suitable at any appropriate temperature such as between about 20° C. and about 50° C., between about 30° C. and about 40° C., or about 37° C. After the tissue is added to a buffer solution, a hydrolase enzyme is added (120). Any suitable enzyme may be used, such as hydrolase enzymes that include ficin, pancreatin, amylases, lipases, and/or various proteolytic enzymes such as pepsin, trypsin, chymotrypsin, and papain, etc. The hydrolase enzyme assists in catalyzing the cleavage of proteins and solubilizing other tissue components and non-collagenous impurities. The enzyme may be kept in solution for an appropriate amount of time for the enzymatic activity to cause telo-peptide bonds to be broken down, which may allow the collagen fibers to unwind, as evidenced by the appearance of strand-like collagen in solution. Any suitable length of time may be used, including time ranging from seconds to minutes to hours or longer. For ficin, the enzymatic activity occurs for about 30 minutes with intermittent stirring. However, the amount of time the enzymatic activity the tissue in solution undergoes may be adjusted so that the collagen fibers preserve their fiber orientation and/or native constituents that may provide potential benefits. For example, by preserving the original or native constituents in collagen, uniquely human collagen characteristics may be provided to the resulting implant, which can result in medical implants dispersing or cross-linking after implantation due to an implantee's biochemical recognition of the medical implant as acceptable.

The enzyme-treated fibers are separated (130) from the enzyme-buffer solution and added (140) to an enzyme deactivation solution selected based on the enzyme used. In one embodiment, where ficin is used, a suitable deactivation solution may be sodium chlorite ($NaClO_2$) in an ammonium nitrate ($NH_4NO_3$) buffer solution. Alternatively, the deactivation solution may be an oxidizing agent such as hydrogen peroxide in a sodium chlorite buffer solution. In addition, use of an oxidizing agent may also facilitate in bleaching the fibers. The tissue is exposed to the deactivation solution for an amount of time sufficient to deactivate the enzyme reaction, for example about 1 hour when the enzyme is ficin. Generally, the enzyme deactivation solution will be a non-alkaline solution, which may be less harsh on the fibers, thereby assisting in retention of the natural collagen constituents. Alternatively, the enzyme may be deactivated in the enzyme solution by changing the temperature or the pH, including raising the pH, of the enzyme solution.

The treated fibers are removed (150) from the deactivation solution and subjected (160) to a series of distilled water washing cycles. Each washing cycle involves washing (161)

the fibers with 500 ml distilled water for a period of about 15 minutes. The tissue is compressed to squeeze out excess water and the pH of the distilled water used in washing the fibers is taken after each wash period (162). The pH after the first and second wash is expected to be about 7.0±0.5, and after a third wash is expected to be about 7.0±0.2. When the pH of the distilled water reaches a desired pH range, e.g., 7.0±0.2, the washing process may be terminated. It will be understood that any suitable pH range can be used for this purpose, including from about 3 to about 9, from about 5 to about 7, or from about 6.0 to about 6.3.

In one embodiment, after washing with distilled water, excess water may be removed from the washed fibers by any suitable method, such as compression or squeezing. For example, fibers may be hand squeezed, pressed onto a fine screen, vacuumed, centrifuged, combinations thereof, etc. Optionally, the fibers may undergo (170) a series of de-watering treatments. Any suitable treatment may be used, including, by way of example only, placing the fibers into a bath of 100% isopropanol (IPA), heating to about 60° C., and blending for about 15 to about 60 seconds. The fibers may remain in the de-watering solution as appropriate, including for about 2 hours at about 60° C., optionally with intermittent stirring. After the first de-watering treatment, the fibers may be separated from the solution, squeezed and subjected to another de-watering treatment, as desired. The subsequent de-watering cycle may be repeated in the same manner. In various embodiments, the time spent by the fibers in the de-watering solution may vary. For example, in subsequent de-watering steps, the fibers may remain in the de-watering solution for about one hour as opposed to about two. In the exemplary use of 100% IPA as the de-watering solution, the IPA, in addition to removing water from the fibers, also may assist in the removal of any oils present in the collagen mixture.

After the de-watering cycles, the fibers are transferred (180) to another bath for removing the de-watering solution. For example, when IPA is the de-watering solution, the fibers may be added to a 100% acetone bath and heated to about 40° C. In addition, the fibers in the bath may be blended for a period of 15 to 60 seconds. Removing the de-watering solution with 100% acetone, in addition to removing alcohols or water, also remove any oils potentially present in the collagen mixture.

The purified fibers may be removed from the bath, separated apart from each other, and dried (190) as appropriate. One suitable drying procedure includes drying at about 40-45° C. for a period of time, such as about 4-12 hours, although any other suitable drying procedure also may be used. The isolated, enzyme treated human collagen fibers in particular embodiments includes natural, native collagen constituents, and may be used for a variety applications including for medical implants. An exemplary process for forming a medical implant using, at least in part, purified human collagen fibers is described below in relation to FIGS. 2A-2F.

The collagen preservation and purification method may be supplemented or steps may be altered to preserve a desired collagen end product. For example, the collagen preparation process may include a terminal sterilization procedure that may include dialysis, irradiation, filtration, chemical treatment, or other suitable procedure. In addition, collagen may be blended at various other points in the recovery process in addition or as an alternative to the blending processes described above. Further, homogenizing the collagen mixture may replace or supplement blending. Moreover, in order to further express water from the fibers after washing with distilled water or after the de-watering step, the collagen fibers may be frozen so that any remaining water is expelled.

The collagen preservation methods of the present application may result in human collagen fibers that are relatively pure, e.g., greater than about 70%, greater than about 80%, greater than about 90%, greater than about 95%, or greater than about 98%. According to the embodiments of the present invention, purified collagen fibers means that the fibers are treated, cleansed, or made suitable for implantation and for use as medical devices using any suitable collagen preparation, preservation, recovery or purification methods, including the methods described above. Purity does not denote any particular degree of purity, and may include a variety of levels of purity, as appropriate for the intended purpose.

In some embodiments, the collagen recovery and preservation method of the present invention does not use an alkali treatment step, and a non-alkaline solution is used for enzyme deactivation. This is useful according to embodiments of the present invention because certain collagen constituents native to humans, e.g., human growth factors and morphogenic proteins that would otherwise be stripped away by exposure to an alkaline solution, are maintained. In addition, because the collagen fibers are derived from humans, harsh purification and/or treatment processes may be unnecessary because human based collagen is less likely to be contaminated as compared to xenogenic tissue. It will be understood that collagen preservation may be accomplished using a variety of methods and may include collagen processing steps in addition to or as an alternative to the processing steps described above.

Moreover, because the collagen fibers are sourced from humans, products formed from these fibers are less likely to produce an immunogenic response when used for implantation into humans. Accordingly, the human collagen recovery method, according to certain embodiments of the present invention, is a simplified method compared to xenogenic collagen recovery methods, and end products made from the human derived collagen fibers are desirable, as they are likely to be accepted at an implant site.

Figure 2A:
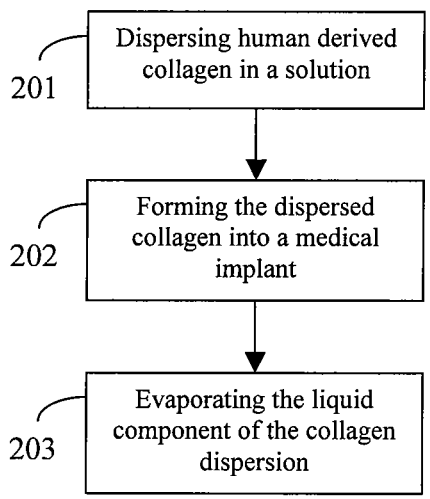
Figure 2B:
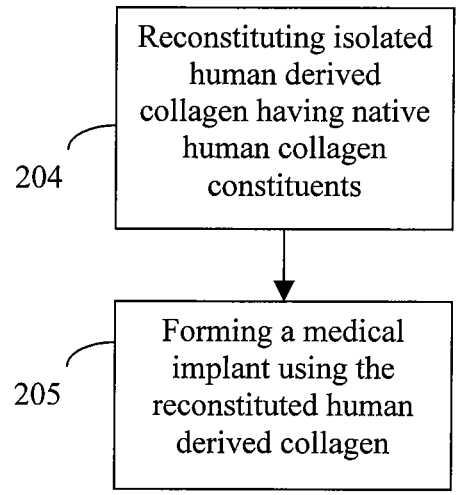

Various medical implants may be constructed using purified human derived collagen. FIG. 2A depicts one method of forming an implant using human derived collagen. According to the embodiment of FIG. 2A, human derived collagen is dispersed (201) in solution, formed (202) into a medical implant, e.g., hemostat, repair matrix/scaffold, drug delivery device, vascular/neural graft, or stent, and the liquid portion of the dispersion is evaporated (203). The implants formed using the method of FIG. 2A may include non-woven collagen textiles or films, for example, and may be used as wound repair patches, as barriers, or as stabilizers. According to a further embodiment, by combining a dispersion of collagen with a biocompatible plasticizer or other component and evaporating the liquid in the composite, desirable implant characteristics may result. For example, desirable implant characteristics may include an implant that has flexibility and is biologically accepted by the host organism, while performing its intended function.

In another example, a medical implant may be formed from reconstituted human derived collagen having its native human constituents preserved. Some forms of human derived collagen may be in a dry or dehydrated form and require rehydrating or reconstituting before use as or in a medical implant. According to FIG. 2B, human derived collagen having native human collagen constituents is reconstituted (204), and the reconstituted collagen is formed (205) into a medical implant. Reconstituting human collagen is described further below in the context of FIG. 2D.

Figure 2C:
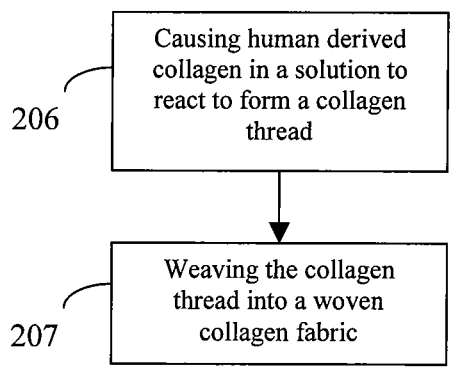
Figure 4:
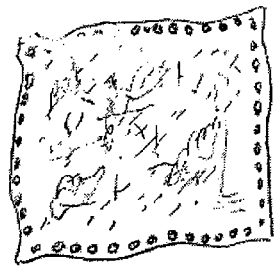
FIG. 4 is an illustration of a non-woven sheet formed using human derived collagen in accordance with an embodiment of the present invention.
Figure 5:
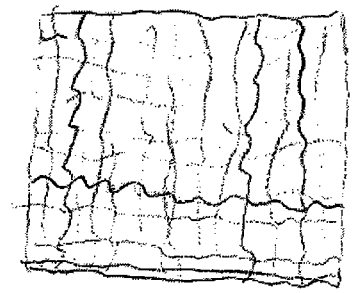
FIG. 5 is an illustration of a woven fabric formed using human derived collagen thread in accordance with an embodiment of the present invention.

In another example, an implant formed using human derived collagen may be in the form of a woven fabric (FIG. 5). FIG. 2C depicts a method for forming a woven fabric using a collagen thread. In FIG. 2C, human derived collagen is caused (206) to react and bind together to form a collagen thread. The collagen thread may be used in any desired manner, including without further processing, or processed into a strand or suture, woven (207) into a woven collagen fabric, or formed into a non-woven material (FIG. 4).

Figure 2D:
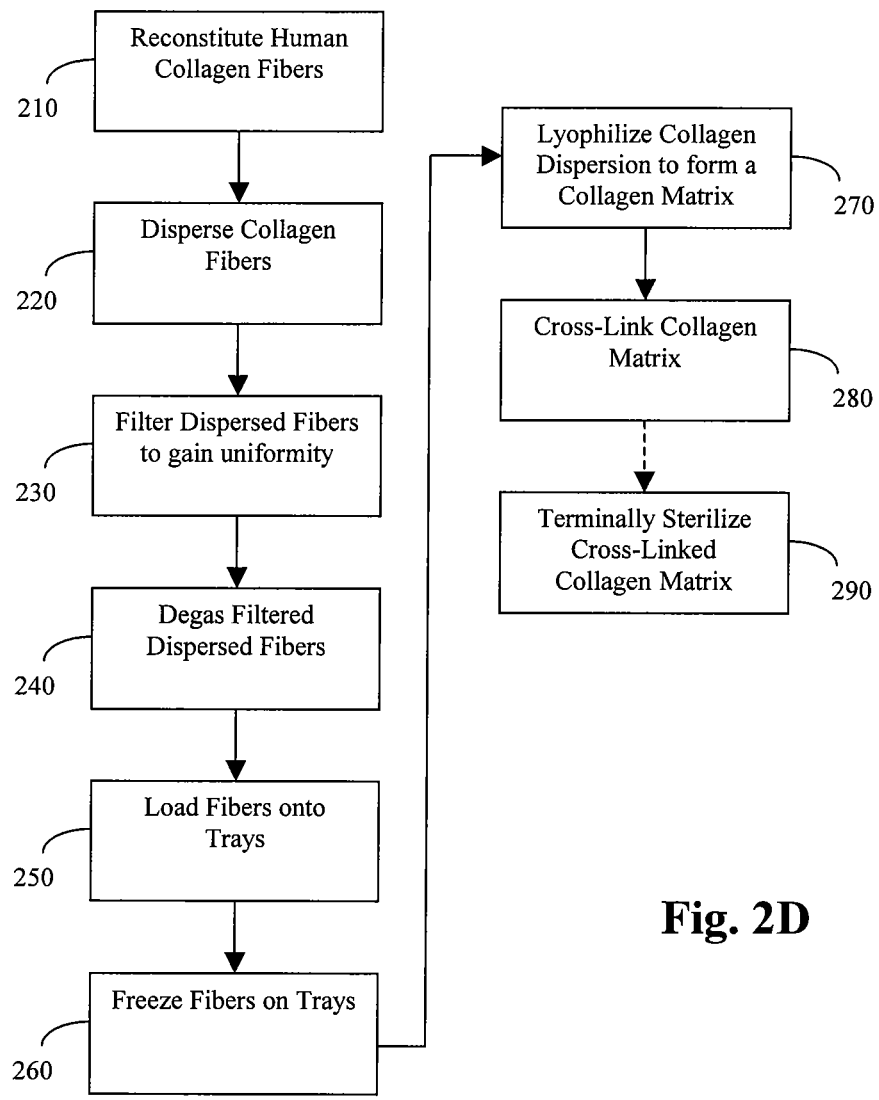
Figure 3:
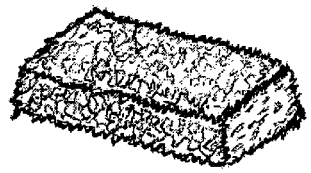
FIG. 3 is an illustration of a wound repair dressing constructed from human derived collagen in accordance with an embodiment of the present invention.

According to certain embodiments, a particular type of implant that may be constructed from human derived collagen is a wound repair matrix (FIG. 3). A method for constructing the wound repair matrix is depicted in FIG. 2D and involves reconstituting (210) human derived collagen fibers by adding the fibers to a media that allows the fibers to become swollen and take up water without denaturing the triple helix structure of the collagen. Any suitable media may be used, including an acidic media. One example of an acidic dispersing media that is suitable for dispersion of the human collagen fibers and their resulting reconstitution when forming a dura/meningeal repair matrix, a particular type of wound repair matrix, is an about 85% lactic acid solution in distilled water at a ratio of about 1:500, where the collagen fibers are permitted to swell for about 1 hour at a temperature of ≤ about 15° C. Any of these parameters may be adjusted as desired for the particular application. The reconstituted collagen in solution may have a dural dispersion of, for example, about 0.5 to about 1.25% collagen density, although any other values can be used, as appropriate.

After reconstitution, a collagen dispersion is prepared (220) by any suitable method. One example of a suitable method includes blending the fibers in solution having a temperature of about 10-15° C. at various speeds for intervals of about 5 to 25 seconds, with a time period of about 30 minutes between blending intervals. Any of these parameters may be varied as dictated by the fiber and density specified by the product under construction. According to the presently described embodiment, the resulting dispersion may have about a 0.75% collagen density at a pH of about 2.8-3.2, though any desired density and pH may be achieved.

The collagen dispersion may be filtered (230), which may enhance uniformity. For example, the dispersion may be filtered through a woven screen mesh having 0.024" round or square openings, through a perforated stainless steel screen having 24 gauge holes that form about a 30% open area, etc. Filtering may be repeated to ensure a uniform dispersion. In some embodiments, the filtering is conducted at a desired temperature, e.g., a temperature of ≤ about 15° C., or any other desired temperature or range of temperatures.

The filtered collagen product may be subsequently degassed (240), which affects the porosity of the finished product. In one example, the collagen product is degassed via centrifugation, which can eliminate large irregular pockets of gas or air. The degassed product may be collected by slow decant while discarding any precipitate, such as dense collagen particles resulting from lactic acid not penetrating interior collagen fibers in a dense fiber bundle or pellet, and the filtered collagen product is or can be loaded (250) into stainless steel trays to a depth ranging from about 2 mm to about 15 mm, depending on the desired product thickness.

The trays loaded with the collagen dispersion product may be frozen (260). For example, the trays may be frozen to a temperature of about −30 to −50° C., e.g., for about 6 hours, to achieve a uniformly frozen dispersion. This may be accomplished in any suitable manner, including by freezing the product in a freezer or lyophilizer.

Once frozen, the collagen dispersion may be lyophilized (270) to maintain the shape and distribution of the collagen sponge matrix while removing the water component of the dispersion. According to certain embodiments, a lyophilizer is programmed to conduct a number of cycles, each cycle having a set temperature, at a given vacuum pressure and for a given period of time. For example, the temperature inside the lyophilization chamber can be in the range of about −30° C. to about 30° C., the vacuum pressure can range from about 90 Millitorr to about 300 Millitorr, and the duration for each cycle may range from about 1 hour to about 10 hours. It will be understood that the cycle parameters may be selected and/or adjusted in order to remove the water component of the collagen dispersion without causing the collagen matrix to collapse or become damaged.

In some embodiments, the lyophilized collagen matrix may be cross-linked (280) to maintain the matrix in a desired form. In certain embodiments, cross-linking may be achieved by exposing the lyophilized collagen matrix to a cross-linking agent in the form of a vapor phase aldehyde gas such as formaldehyde, glutaraldehyde, acetaldehyde, glyoxal pyruvic aldehyde, dialdehyde starch, glycerol polyglycidyl ethers, polyethylene glycol diglycidyl ethers, polyvalent metallic oxides, dicyclohexyl carbodiimide and/or a combination of these. Any suitable cross-linking method may be used. For example, the collagen matrix may be suspended in a vessel holding a volume of aldehyde solution sufficient to cover the bottom of the vessel. The vessel with the matrix suspended inside may be covered for a suitable period of time, e.g., a range of about 15 minutes to 2 hours, to which allow the vapor phase of the aldehyde to cause vapor phase cross-linking. Alternatively, the lyophilized collagen matrix may be cross-linked by dehydrothermal cross-linking, by subjecting the matrix to ultraviolet light, or by any other suitable method.

In some embodiments, the cross-linked collagen matrix may be terminally sterilized (290). Any suitable terminal sterilization method may be used, including ethylene oxide gas treatment, cobalt radiation, electron beam radiation, gas plasma processing, etc. In addition to or as an alternative to sterilizing, the cross-linked collagen matrix may be packaged for subsequent use as a wound repair matrix.

Figure 11:
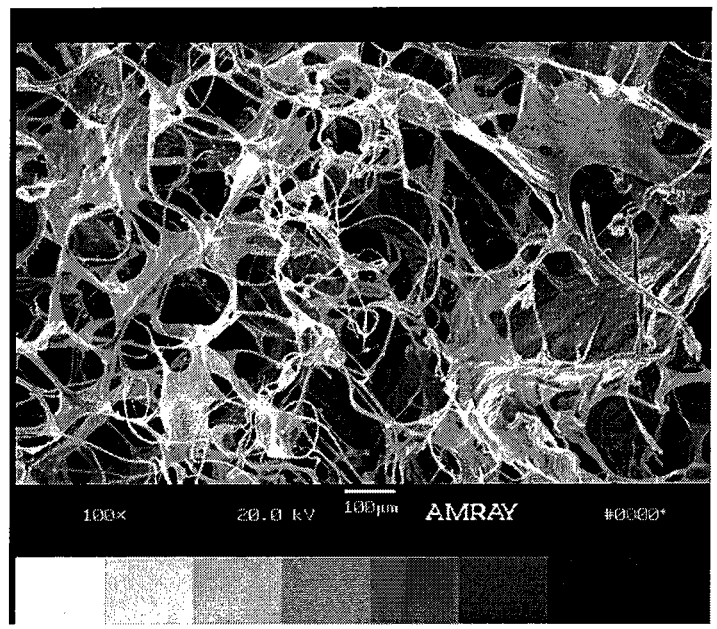
FIG. 11 is a photograph, taken at 100× magnification by scanning electron microscopy, of a collagen sponge made from human fascia that is prepared for use as a medical implant in accordance with certain embodiments of the present invention.

FIG. 11 is a photograph, taken at 100× magnification by scanning electron microscopy, of a collagen sponge made from human fascia that may be prepared according to the method described above in relation to FIG. 2D and used as a medical implant in accordance with certain embodiments of the present invention.

According to alternative methods for forming medical implants, collagen preservation methods and methods for medical implant formation may be combined. According to a particular alternative method, processing collagen fibers may be complete after washing enzymatically treated and deactivated collagen fibers. According to this method, the remaining water in the collagen fibers is analyzed to determine solids and to calculate the dispersion formulation, the fibers dispersed in an acid media and processed according to steps 220-290 in the method described in FIG. 2D.

Wound repair matrices fabricated from the methods described above may have various applications. For example, a wound repair matrix may be used as a dura/meningeal repair dressing, as a sponge-like or absorbent hemostat, or it may be used in combination with other medical implant structures with or without human derived collagen components.

In alternative embodiments, a wound repair matrix or hemostat may be provided that includes fibrillar collagen strands, which may or may not be cross-linked. In another embodiment, wound repair matrices or hemostats may be formed using particulate human derived collagen. Furthermore, wound repair matrices or hemostats may be fabricated as a matrix, with fibrillar collagen strands and/or with particulate human derived collagen.

Other structural repair medical implants may be formed from human derived collagen fibers, and may include an abdominal repair patch for use in repairing an abdominal wall (FIGS. 4 and 5). The repair patch may be fabricated by forming a pliable, non-woven or woven sheet of collagen that can be sutured around the area of the abdomen to be repaired. For example, a non-woven sheet of collagen (FIG. 4) may be constructed according to the method depicted in FIG. 2A, above. Alternatively, a woven sheet of collagen (FIG. 5) may be formed by the method depicted in FIG. 2C.

Figure 6:
FIG. 6 is an illustration of a meniscus or cartilage repair structure formed using human derived collagen in accordance with an embodiment of the present invention.

Other medical implants such as a meniscus or cartilage repair structure (FIG. 6) for use in ligament repair, i.e., in meniscus repair, a sphincter repair matrix, a structural support sling, e.g., a bladder support, or other suitable scaffolding structures for implantation may be formed using one or more of the medical implant methods describe above in relation to FIGS. 2A-2D. Alternatively, the meniscus or cartilage repair structure may be formed, for example, according to the method depicted in FIG. 2E. According to FIG. 2E, the meniscus or cartilage repair structure is formed by depositing (2110) a collagen dispersion in a mold having a desired shape and evaporating (2120) the liquid in the collagen dispersion. In another example, the collagen dispersion is mixed with a suitable biocompatible substance before depositing the dispersion into the mold.

Figure 7:
FIG. 7 is an illustration of a prosthetic coated with human derived collagen in accordance with an embodiment of the present invention.
Figure 8:
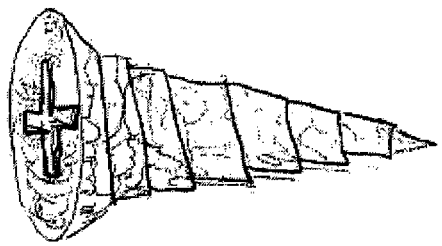
FIG. 8 is an illustration of an implantable instrument coated with human derived collagen in accordance with an embodiment of the present invention.

Collagen fibers derived from humans may also be used as or in coatings. For example, according to the method depicted in FIG. 2F, human derived collagen may be processed (2210) into gelatin and used to coat (2220) implantable medical articles such as prosthetics and instruments. For example, various prosthetics (FIG. 7) and/or instruments (FIG. 8) may be coated with the gelatin formed from the human derived collagen fibers. In a further implementation, a plasticizer or other biocompatible component may be combined with the gelatin formed from human derived collagen in order to cause the gelatin to form a thick paste, slurry, putty, etc.

Figure 9:
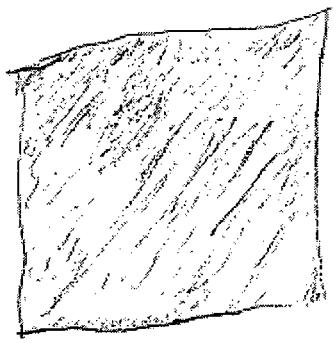
FIG. 9 is an illustration of a film formed with human derived collagen in accordance with an embodiment of the present invention.

Additionally, a film barrier (FIG. 9) may be formed using human derived collagen by, for example, depositing a thin layer of suspended collagen fiber and evaporating the liquid from the suspension, for example by using the method described in FIG. 2A. The resulting sheet may be used as a film, or may be further processed to achieve desired characteristics. In addition, before evaporating liquid from the fiber suspension, other biocompatible materials may also be mixed with the suspension when certain performance characteristics are desirable.

Figure 10:
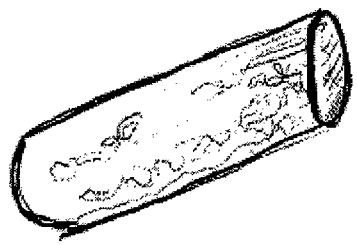
FIG. 10 is an illustration of a vascular graft formed with human derived collagen in accordance with an embodiment of the present invention.

Collagen preserved according to methods of the present invention also may be used in any other suitable context. For example, other applications in which human derived collagen may be used in are vascular (FIG. 10) and neural grafts. Various processing techniques may be employed to construct a tube-like structure that may serve as vascular material. According to an exemplary construction method, a vascular/neural graft is made by adjusting the pH of an acidic dispersion to a more basic condition, resulting in the collagen fibers fully precipitating. The precipitated collagen fibers are firm and entangled, while at least partly suspended in the water media, and can be easily be spun or wrapped onto a dowel or mandrel of a size suitable for reproducing the vascular/neural tissue to be repaired. The wrapped mandrel is frozen, transferred to a lyophilizer and processed. The resulting grafts can then be cross-linked to maintain their shape after removal of the dowel.

The above-described structural implants and method of making the implants that include human derived collagen should not be construed as limiting. For example, products described above, such as the medical repair patch, in addition to or as an alternative to being non-woven or woven, may also be braided and/or knitted, or may a combination of two or more of a non-woven, woven, braided (flat, three-dimensional, etc.), knitted patch, etc. Moreover, although the products described above have associated exemplary applications, other applications for the products are also contemplated. For example, the medical repair patch, in addition to its exemplary use a patch for repairing an opening, also may serve as a barrier for separating portions of the body or as a stabilizer for stabilizing areas of the body. In a further example, the wound repair matrices resembling a sponge or the collagen film may serve as a growth media or substrate.

Furthermore, products incorporating human derived collagen fibers may be designed to include various physical characteristics. For example, structural repair implants having incorporated collagen fibers may be constructed so that the implant is suturable, e.g., where the patch is fabricated to include suture holes in the non-woven fabric seen in FIG. 4, such that the implant can be fixed at an implant site. In addition, medical implants having human derived collagen fibers may be formed as a flexible or rigid implant depending on the implant's intended application.

Moreover, according to certain embodiments, various products having human derived collagen fibers may be combined to form a composite of two or more of the above-mentioned products; and other products not having human derived collagen fibers may also be combined with the various products described herein.

Various modifications may be incorporated into the embodiments disclosed herein. For example, human derived collagen may be mixed with synthetic collagen or other synthetic biocompatible substances in order to achieve a desired product, physical property or performance. In addition, human derived collagen may be processed into putties or pastes so that the implant may be melted and/or shaped for an appropriate implantation use.

In accordance with some embodiments, other additives, including but not limited to those described below, may be added as a supplement to the human collagen. It will be appreciated that the amount of additive used will vary depending upon the type of additive, the specific activity of the particular additive preparation employed, and the intended use of the composition. Any of a variety of medically and/or surgically useful optional substances can be added to, or associated with, the collagen material, at any appropriate stage of the processing.

For example, angiogenesis may be an important contributing factor for the collagen device in certain applications. In certain embodiments, angiogenesis is promoted so that blood vessels are formed at an implant site to allow efficient transport of oxygen and other nutrients and growth factors to the developing bone or cartilage tissue. Thus, angiogenesis promoting factors may be added to the collagen to increase angiogenesis. For example, class 3 semaphorins, e.g., SEMA3, controls vascular morphogenesis by inhibiting integrin function in the vascular system, Serini et al., *Nature*, (July 2003) 424:391-397, and may be included in the collagen device.

In accordance with other embodiments, collagen devices may be supplemented, further treated, or chemically modified with one or more bioactive agents or bioactive compounds. Bioactive agent or bioactive compound, as used herein, refers to a compound or entity that alters, inhibits, activates, or otherwise affects biological or chemical events. For example, bioactive agents may include, but are not limited to, osteogenic or chondrogenic proteins or peptides; demineralized bone powder as described in U.S. Pat. No. 5,073,373; hydroxyapatite and/or other minerals; xenogenic collagen, insoluble collagen derivatives, etc., and soluble solids and/or liquids dissolved therein; anti-AIDS substances; anti-cancer substances; antimicrobials and/or antibiotics such as erythromycin, bacitracin, neomycin, penicillin, polymycin B, tetracyclines, biomycin, chloromycetin, and streptomycins, cefazolin, ampicillin, azactam, tobramycin, clindamycin and gentamycin, etc.; immunosuppressants; anti-viral substances such as substances effective against hepatitis; enzyme inhibitors; hormones; neurotoxins; opioids; hypnotics; anti-histamines; lubricants; tranquilizers; anti-convulsants; muscle relaxants and anti-Parkinson substances; anti-spasmodics and muscle contractants including channel blockers; miotics and anti-cholinergics; anti-glaucoma compounds; anti-parasite and/or anti-protozoal compounds; modulators of cell-extracellular matrix interactions including cell growth inhibitors and antiadhesion molecules; vasodilating agents; inhibitors of DNA, RNA, or protein synthesis; anti-hypertensives; analgesics; anti-pyretics; steroidal and non-steroidal anti-inflammatory agents; anti-angiogenic factors; angiogenic factors and polymeric carriers containing such factors; anti-secretory factors; anticoagulants and/or antithrombotic agents; local anesthetics; ophthalmics; prostaglandins; anti-depressants; anti-psychotic substances; anti-emetics; imaging agents; biocidal/biostatic sugars such as dextran, glucose, etc.; amino acids; peptides; vitamins; inorganic elements; co-factors for protein synthesis; endocrine tissue or tissue fragments; synthesizers; enzymes such as alkaline phosphatase, collagenase, peptidases, oxidases, etc.; polymer cell scaffolds with parenchymal cells; collagen lattices; antigenic agents; cytoskeletal agents; cartilage fragments; living cells such as chondrocytes, bone marrow cells, mesenchymal stem cells; natural extracts; genetically engineered living cells or otherwise modified living cells; expanded or cultured cells; DNA delivered by plasmid, viral vectors, or other means; tissue transplants; autogenous tissues such as blood, serum, soft tissue, bone marrow, etc.; bioadhesives; bone morphogenic proteins (BMPs); osteoinductive factor (IFO); fibronectin (FN); endothelial cell growth factor (ECGF); vascular endothelial growth factor (VEGF); cementum attachment extracts (CAE); ketanserin; human growth hormone (HGH); animal growth hormones; epidermal growth factor (EGF); interleukins, e.g., interleukin-1 (IL-1), interleukin-2 (IL-2); human alpha thrombin; transforming growth factor (TGF-beta); insulin-like growth factors (IGF-1, IGF-2); parathyroid hormone (PTH); platelet derived growth factors (PDGF); fibroblast growth factors (FGF, BFGF, etc.); periodontal ligament chemotactic factor (PDLGF); enamel matrix proteins; growth and differentiation factors (GDF); hedgehog family of proteins; protein receptor molecules; small peptides derived from growth factors above; bone promoters; cytokines; somatotropin; bone digesters; antitumor agents; cellular attractants and attachment agents; immunosuppressants; permeation enhancers, e.g., fatty acid esters such as laureate, myristate and stearate monoesters of polyethylene glycol, enamine derivatives, alpha-keto aldehydes, etc.; and nucleic acids.

In certain embodiments, the bioactive agent may be a drug. In some embodiments, the bioactive agent may be a growth factor, cytokine, extracellular matrix molecule, or a fragment or derivative thereof, for example, a cell attachment sequence such as RGD. A more complete listing of bioactive agents and specific drugs suitable for use in the present invention may be found in "Pharmaceutical Substances: Syntheses, Patents, Applications" by Axel Kleemann and Jurgen Engel, Thieme Medical Publishing, 1999; the "Merck Index: An Encyclopedia of Chemicals, Drugs, and Biologicals", Edited by Susan Budavari et al., CRC Press, 1996; and the United States Pharmacopeia-25/National Formulary-20, published by the United States Pharmcopeial Convention, Inc., Rockville Md., 2001.

In some embodiments, the agent to be delivered may be adsorbed to or otherwise associated with the human collagen. The agent may be associated with the collagen through specific or non-specific interactions, covalent or non-covalent interactions, etc. Examples of specific interactions include those between a ligand and a receptor, an epitope and an antibody, etc. Examples of non-specific interactions include hydrophobic interactions, electrostatic interactions, magnetic interactions, dipole interactions, van der Waals interactions, hydrogen bonding, etc. In certain embodiments, the agent may be attached to the collagen using a linker so that the agent is free to associate with its receptor or site of action in vivo. In other embodiments, the agent may be bound or captured within the collagen as a result of collagen cross-linking. In certain embodiments, the agent to be delivered may be attached to a chemical compound such as a peptide. In another embodiment, the agent to be delivered may be attached to an antibody, or fragment thereof, that recognizes an epitope found within the collagen. In certain embodiments, at least two bioactive agents may be attached to the collagen. In other embodiments, at least three bioactive agents may be attached to the collagen. Sebald et al., PCT/EP00/00637, describes the production of exemplary engineered growth factors that are beneficial for use with the collagen device.

The above description should not be construed as limiting, but merely as exemplifications of, preferred embodiments. Those skilled in the art will envision other modifications within the scope and spirit of the present disclosure.

What is claimed is:

1. A medical implant comprising isolated, enzymatically-treated human derived collagen having a preserved amount of its natural collagen constituents, wherein the enzyme treatment comprises digesting the collagen with ficin and deactivating the ficin with a non-alkaline sodium chlorite solution to maintain growth factors and morphogenic proteins otherwise stripped away by exposure to an alkaline solution, wherein the collagen is lyophilized by exposing the collagen to a vapor phase cross-linking agent, the cross-linking agent comprising at least one of acetaldehyde, dialdehyde starch, glycerol polyglycidyl ethers, polyethylene glycol diglycidyl ethers, polyvalent metallic oxides, or a combination thereof, wherein the collagen comprises cartilage fragments, a plasticizer and angiogenesis promoting factors, the angiogenesis promoting factors comprising SEMA3.

2. The medical implant of claim 1, wherein the collagen is fibrillar human derived collagen.

3. The medical implant of claim 1, wherein the collagen is particulate human derived collagen.

4. The medical implant of claim 1, wherein said implant comprises a wound repair matrix.

5. The medical implant of claim 1, wherein said implant comprises an absorbent hemostat.

6. The medical implant of claim 1, wherein said implant comprises a medical repair patch.

7. The medical implant of claim 6, wherein the medical repair patch is a woven patch.

8. The medical implant of claim 6, wherein the medical repair patch is a non-woven patch.

9. The medical implant of claim 6, wherein the medical repair patch is a braided patch.

10. The medical implant of claim 6, wherein the medical repair patch is a film patch.

11. The medical implant of claim 6, wherein the medical repair patch is a knitted patch.

12. The medical implant of claim 6, wherein the medical repair patch is at least two of a woven, a non-woven, a braided, a film, and a knitted patch.

13. The medical implant of claim 1, wherein said implant comprises a vascular graft.

14. The medical implant of claim 1, wherein said implant comprises a neural graft.

15. The medical implant of claim 1, wherein said implant comprises a sphincter repair matrix.

16. The medical implant of claim 1, wherein said implant comprises a film.

17. The medical implant of claim 1, wherein said implant comprises a prosthetic having a coating of the enzymatically-treated human derived collagen.

18. The medical implant of claim 1, wherein said implant comprises an implantable instrument having a coating of the enzymatically-treated human derived collagen.

19. The medical implant of claim 1, wherein said implant comprises a structural support sling.

20. The medical implant of claim 1, wherein said implant comprises a bioactive agent.

21. A medical implant comprising: reconstituted human derived collagen, wherein the human derived collagen comprises a preserved amount of its native collagen constituents of growth factors and morphogenic proteins, wherein the collagen is lyophilized by exposing the collagen to a vapor phase cross-linking agent, the cross-linking agent comprising at least one of acetaldehyde, dialdehyde starch, glycerol polyglycidyl ethers, polyethylene glycol diglycidyl ethers, polyvalent metallic oxides, or a combination thereof, wherein the collagen comprises cartilage fragments, a plasticizer and angiogenesis promoting factors, the angiogenesis promoting factors comprising SEMA3, and the medical implant comprises a cartilage repair structure.

* * * * *